United States Patent [19]

Barabino et al.

[11] Patent Number: 4,740,194

[45] Date of Patent: Apr. 26, 1988

[54] SELF-CONTAINED LIQUID SWAB APPLICATOR AND METHOD FOR ITS MANUFACTURE

[76] Inventors: William A. Barabino, 19 Sunset Ave., No. Reading, Mass. 01864; Raymond S. Dean, 49 Harmon St., Lynn, Mass. 01905

[21] Appl. No.: 905,967

[22] Filed: Sep. 11, 1986

[51] Int. Cl.$^4$ ............................................ A61M 35/00
[52] U.S. Cl. ...................................... 604/3; 604/310; 401/138; 401/196
[58] Field of Search .................. 604/1, 2, 3, 306, 310, 604/244, 213, 214; 401/132, 136, 137, 138, 196

[56] References Cited

U.S. PATENT DOCUMENTS

| | | | |
|---|---|---|---|
| 257,293 | 5/1882 | Cory et al. | 401/139 |
| 2,864,118 | 12/1958 | Adams et al. | 401/132 |
| 3,324,855 | 6/1967 | Heimlich | 604/3 |
| 3,369,267 | 2/1968 | Friedland et al. | 401/132 |
| 3,453,661 | 7/1969 | Repko | 401/132 |
| 3,486,666 | 12/1969 | Herzig | 401/132 |
| 3,757,782 | 9/1973 | Aiken | 401/196 X |
| 3,958,571 | 5/1976 | Bennington | 604/3 |
| 4,127,339 | 11/1978 | Malacheski | 401/132 |
| 4,140,120 | 2/1979 | Yamauchi | 604/213 |
| 4,206,843 | 6/1980 | Rainey | 604/3 |
| 4,291,697 | 9/1981 | Georgevich | 604/3 |

*Primary Examiner*—C. Fred Rosenbaum
*Assistant Examiner*—Denise Whelton
*Attorney, Agent, or Firm*—Richard C. Litman

[57] ABSTRACT

A self-containing liquid swab applicator having a hollow tubing of a thin-walled plastic material for retaining therein a supply liquid and the material for being heat fusible, at least one end thereof being closed for securing retention of the supply liquid, one of the ends having an orifice adapted for exiting of the supply liquid, removable tab means secured upon the orifice for closure of the orifice until removed, and cotton form means permitting wicking and forming an environmental member about the orifice portion of the swab applicator for dispensing the supply liquid when the orifice is opened. The open end(s) may receive sequentially pulsing of alternate injections of supply liquid and air into one end of the tubing in measurable amounts and forming liquid lock portions and air lock portions along the tubing, and defining N segments of supply liquid spaced apart by air locks, and the segments may be cut apart at the air locks.

10 Claims, 2 Drawing Sheets

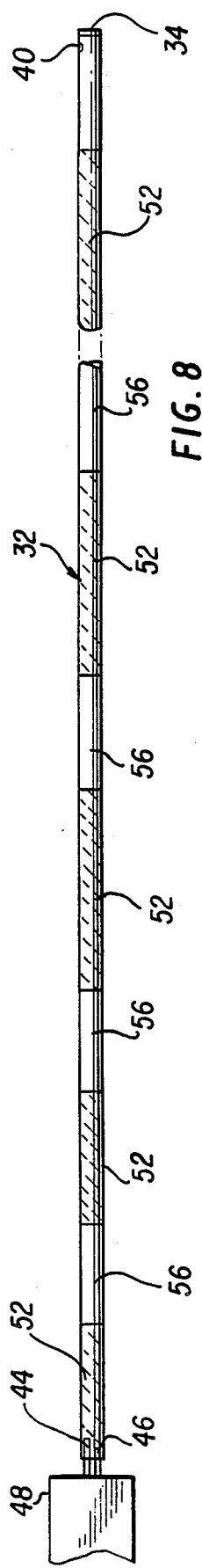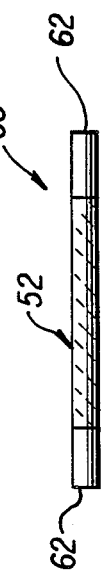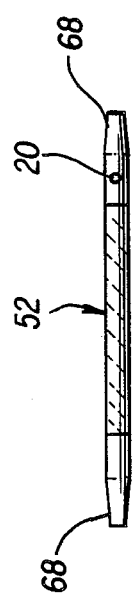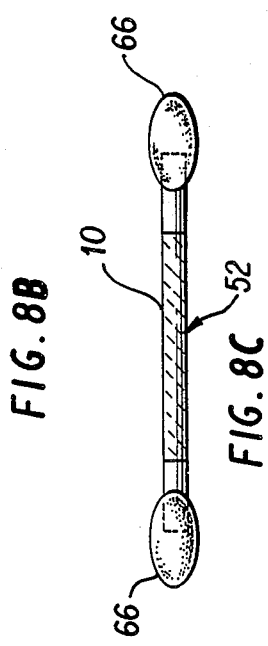

SELF-CONTAINED LIQUID SWAB APPLICATOR AND METHOD FOR ITS MANUFACTURE

BACKGROUND OF THE INVENTION

Field of the Invention

The invention relates to an improved self-containing liquid swab applicator and its method for filling lengths of tubing with sequential segments of liquid and air, then cutting the tubing at the air segment portion(s) to form separate swab applicators thereby, and more particularly the invention is directed to medical swab structures having a hollow tubing throughout in which the hollow tubing performs as the reservoir for a contained supply liquid and has a formed-cotton member on one or both of its ends. The liquid is uniquely released to the peripheral areas of the tubing structure and this initiates wicking of the liquid from the outer surface to the formed-cotton member to result in more available solution for application from the saturated member.

Descriptions and references to swabs or swab applicators, unless otherwise noted, will generally refer to a swab applicator of the type identified as the household swab applicators whose tubing length is a nominal 75 mm and whose general use would be for the supply liquids such as listed in Category 1 of Table 1.

Many supply liquids are best applied to a surface by the use of a swab applicator that is normally saturated in a supply source of liquid. Their uses are predominantly in the application of topically applying antiseptics, but may also be used as cleaning instruments whereby the cotton-formed end initially acts as the carrier of a solvent or dissolving agent, then secondarily functions as the collector of debris. Insufficient transporting capability encourages a re-submergence into the supply source. This is an unacceptable practice because in the case of home first-aid, for example, it does not protect the supply source from being contaminated with spore-forming bacteria. This practice should not be treated lightly because most home first-aid tinctures of antiseptics have conditioned the user to this practice by supplying a community applicator wand attached to the cover of the supply bottle.

The invention relates further to a device providing for the outward flow of liquid in a self-contained liquid swab applicator and the method of filling the supply tubing thereof as more particularly described herein.

Description of the Prior Art

Various prior art swab applicator devices, and the like, as well as apparatus and method of their construction in general, are found to be known and exemplary of the U.S. prior art are the following:

| | |
|---|---|
| 2,333,070 | Hoey |
| 3,757,782 | Aiken |
| 3,759,259 | Truhan |
| 3,958,571 | Bennington |
| 4,173,978 | Brown |
| 4,218,155 | Weidner |

Bennington discloses merely a free-ended cap that is not resistant to evaporation and suggests an open end member being embedded in cotton. This results in total evaporation of any alcohol tincture in approximately a 24 hour period. The other patents illustrate known configurations of ampoules, some of crushable glass and all require internal saturation of the cotton formed applicator before any liquid may be available to be applied or transferred to a desired surface.

Disposable iodine sticks find replete uses in medical field as a pre-operative preparation and the like. The routine swab, as empirically envisioned, is undercapacitated to deliver a sufficient amount of antiseptic in such instances. Therefore, a heavily oversized iodine swab is hermetically packaged. This is because excess antiseptic is packaged to insure an adequate supply of iodine to be carried by a single swab stick. The user is directed to open the packet at the free-stick end which is only slightly less messy than opening the cotton end.

In a domestic environment dry swabs are used for cleaning infant nostrils and ears. The general populace also use them for ear hygiene to include removal of ear cerumen. These uses are not specifically condoned by the medical profession because the rigidity of solid swab shaft or solid swab tubing may cause serious injury as the result of a sudden or unexpected movement between the user and the swab. Further, when using a swab as a liquid carrier that has a low viscosity, it is not uncommon to be confronted with an oversoaked condition. This is due to the viscosity of the liquid, tightness of cotton winding and the wicking ability of the grade of cotton.

These patents or known prior uses teach and disclose various types of swab devices of sorts and of various manufactures and the like as well as methods of their construction, but none of them whether taken singly or in combination disclose the specific details of the invention in such a way as to bear upon the claims of the present invention.

SUMMARY OF THE INVENTION

An object, advantage and feature of the invention is to provide a novel, self-contained liquid swab applicator and method for its manufacture.

Another object of the invention is directed further to a device providing for the peripheral flow or outward flow of supply liquid in a self-contained liquid swab applicator and the method of initially filling the supply tubing thereof.

Also an object of the invention is to provide a simple and direct method for the improved construction of a swab applicator that overcomes each and every objection above stated.

Another object of the invention is to provide a novel and improved method of selectively making the swab to overcome the heretofore unsolvable problem of economically producing a swab that self-carries a supply liquid and the method of its construction.

These together with other objects and advantages which will become subsequently apparent reside in the details of the process and operation thereof as more fully hereinafter is described and claimed, reference being had to the acompanying drawings forming a part hereof, wherein like numerals refer to like parts throughout.

DESCRIPTION OF THE SEVERAL VIEWS OF THE DRAWINGS

FIGS. 8 to 8C show the steps in manufacture of the swab.

DESCRIPTION OF A PREFERRED EMBODIMENT OF THE INVENTION

Figure 1:
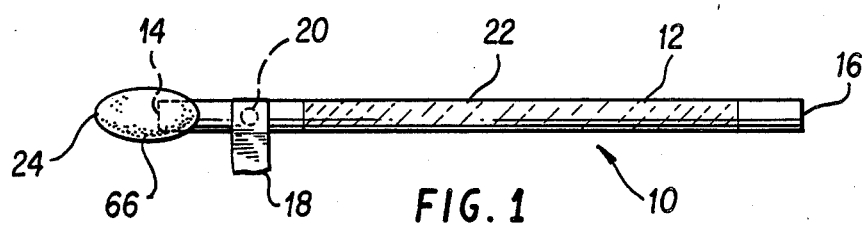
FIG. 1 is a self-contained liquid swab applicator and illustrating a typical installation of the swab according to a preferred embodiment and best mode of the present invention.

Referring now to the drawings there is shown in FIG. 1 a self-containing liquid swab applicator 10 constructed of a hollow flexible plastic material and forming a supply liquid-containing shaft or tubing 12 and shown prepared for use. Sealed ends 14, 16 are sealed and upon removal of an adhesive tape or tab 18, the liquid 22 gravitates through an exit orifice 20 to saturate an outer surface of an adsorbent material 24 forming a swab 66, an open cell foam material or cotton form having a good quality of wickability or one that is found to permit wicking of the supply liquid that thoroughly saturates the outer surface thereof.

The invention will best be understood if the method of filling the tubing is first described because the physical behavior of the liquid and the actual use of the ultimate swab applicator are completely interrelatd in the construction and method thereof. A familiarity with manufacturing techniques and fluid (liquid and gas) physics will readily provide a grasp of the simplicity of the tubing filling procedure and the principles that permit its practicality. All values for dimensions and quantities are nominal and are cited for advisory and reference purposes. There are no critical instances where qualitative judgments, such as amounts of liquid desired on the cotton form 66, cannot be substituted for the quantitative values. Similarly the numerical values assigned to the swab applicators for the fluids tested in Table 1 are the result of experimental investigations. In this case, it is found the relativistic inner action of the liquid quantity, i.e., weight, and the viscosity permit a number of these satisfactory combinations. Generally, the liquids are selectively a water solute, an alcohol solution or a petroleum base.

Referring now to FIG. 8 of the drawings, there is exemplary shown a near non-wettable supply of polypropylene thermoplastic tubing 32 having a thin wall of 0.010 inches and an internal diameter (ID) of 0.125 in., and that may be filled in any manageable and convenient length thereof, whether the tubing 32 is lineal or coiled. A first free-end 34 is heat fused closed and back-pressure relief orifice 40 is made proximate to it. The relief orifice 40 is provided to permit air to escape from the tube as the alternate air and fluid sections are pumped in. Free-end 42 is adapted to receive a liquid injector 44 having an internal diameter of 0.018 in. and an air injector 46 having an internal diameter of 0.018 in. Both injectors are integral in a housing 48 that need be only lightly pressure-sealed against free-end 42. Liquid injector 44 is non-wettable and is provided with a 0.250 in. length dimension over the length of the air injector 46. The liquid injector 44 is pulsed under pressure or vacuum to deliver 0.150–0.200 cc of liquid which are shown as N liquid segments 52. Air injector 46 then sequentially injects air for exerting or pushing the N liquid segments 52 forward each approximately 0.750 in. as show in phantom in FIG. 8. This sequential procedure is repeated until the tubing is fully utilized with the N liquid segments 52 each separated by air locks 56. Use of a pulsed evacuation or vacuum pump (not shown) may be provided at the free-end 34 and may be substituted for the function of the air injector 46. Since the relief orifice relieves the back-pressure in the tubing 32, very little air pressure is required by air injector 46 to push, by selection of pressure means or vacuum means, the N liquid segments 52 separated by air segments 56 along the length of the tubing 32. Regardless of the number of the N segments 52, all quantities and dimensions of liquid and air portions or segments are generally consistent and remain unchanged absolutely and relative to each other throughout the length of the tubing 32.

Table 1 shows results of experimental investigations using supply liquids, or also recognized in some instances in the art as solutions, in three categories of tubing diameters, and with the exception of Category 3, may collectively be accomodated by the described filling procedure using polypropylene tubing 32 having an ID of up to 0.130 in. All are found to have demonstrated within the terms defined by the laws of physics a relatively flat miniscus having contact angles between 75°–95° and correspondingly no minimal rise h.

TABLE 1

| Solution | TESTED LIQUIDS | |
|---|---|---|
| | Main Vehicle | Application |
| Category 1 | | |
| For: | Liquid Injector | 0.008–0.010 in ± 0.002 |
| | Exit Orifice | 0.010 in ± 0.002 |
| | Tubing Capacity | 0.15–0.20 cc ± arbitrary |
| | Tubing Length | 75 mm nominal |
| | Tubing ID | 0.080–0.085 in. |
| Iodine Tincture | Alcohol | Topical Antiseptic |
| Bactine | Alcohol | Topical Antiseptic |
| Merthialate Tincture | Alcohol Water | Topical Antiseptic |
| Mercurochrome | Water | Topical Anitseptic |
| Ambesol | Alcohol | Oral Antiseptic |
| Hydrogen Peroxide | Water | Local Antiseptic |
| Betadene | Water | Topical Antiseptic |
| Gentian Violet | Water | Topical Antimicrobial |
| Gentian Violet | Alcohol | Topical Antimicrobial |
| — | Isopropyl | Topical Antiseptic |
| Kanka | Buffered | Oral Antiseptic |
| Cutex | Acetone | Nail Enamel Remover |
| — | Isopropyl | Audio & Video Devices Head Cleaner |
| Hoppes No. 9 | Petroleum Distillate | Dissolve Gun Chamber Powder |
| Breakfree | Petroleum Distillate | Metal Preservative |
| Household Oil | Petroleum Derivative | Lubrication |
| Category 2 | | |
| For: | Liquid Injector | 0.008–0.-15 in. ± 0.002 |
| | Exit Orifice | 0.010 in ± 0.002 |
| | Tubing Capacity | 2 cc ± arbitrary |
| | Tubing Length | 110 mm ± arbitrary |
| | Tubing ID | 0.160 in. |
| Titratable Iodine | Alcohol | Pre-op Scrub |
| Category 3 | | |
| For: | Liquid Injector | 0.015 in ± 0.002 |
| | Relief Orifice | 0.020 in ± 0.002 |
| | Tubing Capacity | 3 cc ± arbitrary |
| | Tubing Length | 110 mm ± arbitrary |
| | Tubing ID | 0.230 in. |
| Calamine Lotion* | Water | Topical Protective |

*Calamine Lotion is a relatively thick suspension that separates upon standing. Values given are approximately minimal to permit mixing by shaking prior to use.

The physical principle upon which the N segments 52 may be produced is based on the laws of physics as they relate to surface tension of the given liquid, the principle that will continue to be utilized in the fabrication of the swab applicator 10 as well as in its actual uses.

Upon filling to completion of the supply tubing 32, the relief orifice 40 is sealed and the filled tubing may be translocated with the free-end 34 sealed. Sealing of the free-end 42 will result in all segments being locked in absolute position. No orientation of the supply tubing will affect movement of the N segment(s) 52. Non-sealing of 42 results in all N segments 52 moving relatively to each other therein and thus will only occupy any excess tubing 32 when jolted during relocation. However, surface tension at free-end 42 will disallow any liquid to be expelled. The tubing will ultimately be severed or cut into swab lengths at the midpoint of the air locks 56 in a sequence that utilizes surface tension as a fundamental requirement.

By way of example in this description, a segment 60 shown in FIG. 8A will be taken as typical and accordingly referred to in reference to a more detailed description thereof.

Figure 2:
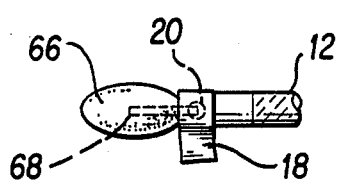
FIGS. 2 to 7 are variations of the swab of FIG. 1 and embodying the concepts of the invention.
Figure 3:
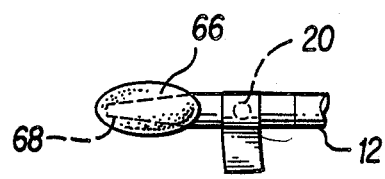

Commencing at either free end of the tubing, after cutting through the tubing at the midpoint of the airlocks 56 as shown in FIG. 8, newly formed free-ends 62 are heat-fused shut, being sealed preferentially by a cylindrical clamping iron (not shown) and resulting in providing a support structure for a cotton form 66 as shown in FIGS. 8C and 2. However, within the purview of the present invention it has been found that using a vise, squeeze-forming iron, ultrasonic welding, radio energy heat sealing as well as other known methods of sealing methods (not shown) may be used to provide a generally flattened terminal 68 as shown in FIG. 8B. The exit orifice 20 as shown in FIG. 8B is then cold punched at a point nearly proximate to the liquid limit and tape sealed to provide the adhesive tab 18 of FIG. 8C. A plastic tape of Scotch Brand No. 191 is found to be essentially immune to adhesive deterioration by vapors of any liquid shown in Table 1. Another segment 60 is then cut midway through the next sequential air lock 56.

A 75 mm tubing acting as a reservoir for 0.15-0.20 cc of liquid will have approximately 16 mm of air space on either end of the liquid segment 52, FIGS. 8B and 8C. Considering the cotton form 66 requires 12 mm of tubing length for support, there remains a nominal 4-5 mm between the termination of the limits of the cotton form 66 on the outside of the tubing and the beginning of the liquid segment 52 on the inside of the tubing. Because of the previously stated effects of surface tension, liquid 22 will not tend to seek the lowest level within the tubing 12. Upon removal of adhesive tab 18 from the orifice 20, the liquid 22 will proceed to flow through orifice 20, but internally never below or beyond it. Referring to the surface tension of water and ethyl alcohol at 20° C. to be 72.8 and 21.7 dynes per cm respectively, a qualitative determination may be made as to the behavior of any liquid attempting to surpass orifice 20 internally. This inability to proceed beyond the orifice is the result of the surface tension being reinforced by the non-wettable polypropylene which disallows the liquid to override the orifice or space obstruction. This feature results essentially in no unusable liquid 22.

Upon removal of tab 18 liquids 22 having an alcohol vehicle of Table 1 are found to flow freely through the orifice 20 for approximately one half of their total volume the balance thereof being squeezably discharged. The balance of the liquids 22 having a water vehicle will generally, depending of course on solutes therein, require squeezable pressure for discharge of any substantial volumes. This aspect of the present invention allows or permits the regulation of the amount of liquid on the end of the cotton form 66.

Surface areas at each termini of the liquid contained in tubing 12 are minimal and result in surface region pressures and vapor pressures rapidly equilibrating. This results in a mathematical, but immeasurable loss of liquid due to evaporation.

The tubing 12 is preferentially constructed of clear or translucent polypropylene material(s) to aid in the sighting of available or remaining liquid. The sealing tab 18 is color-coded and appropriately imprinted with a content description.

Figure 4:
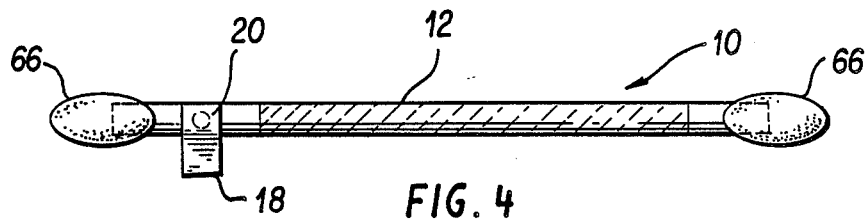
Figure 5:
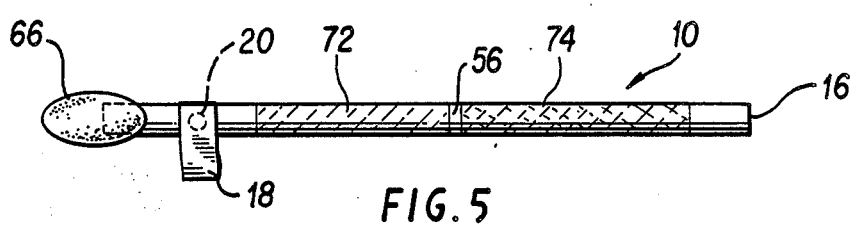
Figure 6:
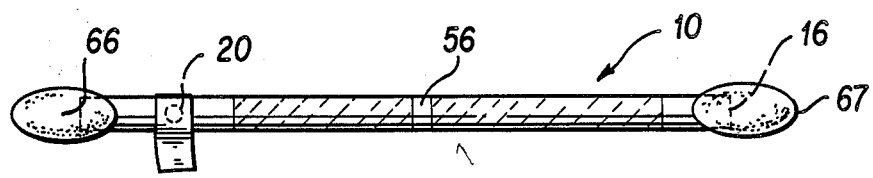

Various combinations of the basic design are apparent within the teachings of the present invention. FIG. 4 depicts a swab applicator 10 and having an additional cotton form 66 at its end. FIG. 5 shows an embodiment of the device wherein two different solutions such as alcohol 72 and water 74 may be separated by an air segment and contained in the tube 12. A second set of injectors (not shown) is provided and programmed to deliver a first liquid, an air segment, a second liquid and another air segment and then to repeat the process until the tube is filled. The tube is then severed at alternate air segments to provide the embodiment of the device as shown. If the evacuation pump technique is used, then only a second liquid injector is required. The liquids are separated by a nominal ±0.125 air lock. For example, a personal hygiene swab applicator 10 adapted according to the teaching of the present invention may be used for ear hygiene, and may contain both alcohol and water. Upon removal of the tab 18 the tube is squeezed to deliver alcohol to the cotton form 24 for use in softening and partial removal of cerumen from the ear. As the level of alcohol drops in the tubing, the air locks 56 and water 74 segments follow. The second solution is not available to the exit orifice 20 until no miniscus of the first fluid remains within the tubing 12. A two stage swab applicator is useful in this application because SD alcohol is found an ideal agent for softening and dissolving ear cerumen; however, it does possess an astringent effect on the inner lobe epithelial. The second solution of water 74 dilutes the surface alcohol eliminating this irritant-like effect. FIG. 6 is a variation of FIG. 5 having a second cotton form 67 for providing a final wiping or drying step.

Figure 7:
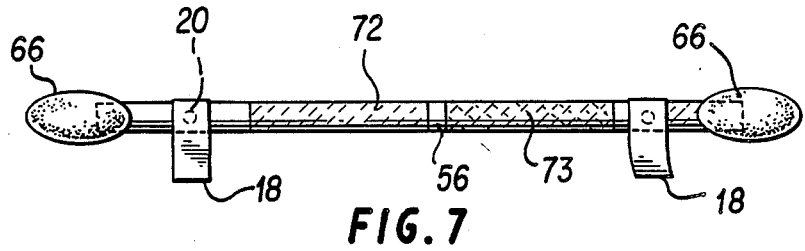

The separation of two liquids on the cotton form in such an application is found not critical, but in those instances where two liquids are required, and their separation must be maintained, an arrangement may be provided as shown in FIG. 7. Procedurally, a punch biopsy epidermal surface is initially bathed with tritrateable iodine or the like, then rinsed with alcohol to prevent the incursion of iodine in the dermal layer by the punch. FIG. 7 shows a variation with second exit orifice 20 and a second cotton form 66 for the second liquid 73.

The liquid of Category 3 of Table 1 is properly classifiable as a separable suspension and as such is limited to the greater nominal ID indicated to allow shaking prior to removal of the tape or tab 18 from the exit orifice 20.

As generally described above and further within the scope of the invention, rigid swab applicators of the prior art such as used for personal hygiene in an an area of the nose and ears, and perhaps elsewhere, are generally discouraged by the medical community and the present invention provides a thin-walled flexible swab applicator that may 'give' before serious injury may result from unexpected and sudden movements. It is however sufficiently rigid to accept lateral forces normally encountered in use.

The foregoing is considered as illustrative only of the principles of the invention. Further, since numerous modifications and changes will readily occur to those skilled in the art, it is not desired to limit the invention to the exact construction and operation as shown and described, and accordingly, all suitable modifications and equivalents may be resorted to falling within the scope of the invention.

What is claimed and desired to be secured by Letters Patents is:

1. A self-contained liquid swab applicator comprising;
   a length of hollow thin-walled tubing of resilient plastics material having two ends, a supply liquid disposed therein, the surface of said material exhibiting an enhanced degree of non-wettability relative the supply liquid,
   means closing said tubing ends to secure retention of said supply liquid therebetween, said closing means adapted to remain intact upon squeezing of said tubing,
   said tubing provided with an orifice extending through its periphery and spaced from one said end for outward flow of the supply liquid upon squeezing of said tubing,
   removable tab means normally overlying said orifice,
   means permitting wicking and defining a swab member mounted upon one said tubing end adjacent said orifice whereby,
   removal of said tab means exposes said orifice and allows the supply liquid to issue through said orifice and migrate along the periphery of said tubing to the periphery of said swab member upon squeezing of said tubing, and upon relaxing the squeezing action, contaminated would fluid is prevented from being sucked into the tubing orifice.

2. The apparatus of claim 1 wherein the removable tab means is adhesively secured about a surface portion adjacent the orifice.

3. The apparatus of claim 1 wherein the removal tab means is frictionally secured about a surface portion adjacent the orifice, and upon its removal, provides for the outward flow of the supply liquid.

4. The apparatus of claim 1 wherein,
   said hollow tubing includes a plurality of masses of said supply liquid, and each adjacent pair of said masses separated by a segment defining an air lock portion.

5. The apparatus of claim 4 wherein the liquid masses are comprised of diverse liquids.

6. The apparatus of claim 4 including, one said orifice disposed adjacent each said tubing end.

7. The apparatus of claim 1 wherein, said closing means comprises heat fused ends.

8. The apparatus of claim 1 wherein, said supply liquid as issued through said orifice is regulated by the squeezing of said tubing.

9. The apparatus of claim 1 wherein, both said tubing ends are provided with one said swab member.

10. The apparatus of claim 1 wherein, said swab member comprises an open cell foam material.

* * * * *